United States Patent
Borsdorf et al.

(10) Patent No.: US 9,549,710 B2
(45) Date of Patent: Jan. 24, 2017

(54) METHODS FOR UPDATING 2D/3D REGISTRATION ON MOVEMENT AND COMPUTING DEVICE

(71) Applicants: Anja Borsdorf, Erlangen (DE); Benno Heigl, Coburg (DE); Jian Wang, Erlangen (DE)

(72) Inventors: Anja Borsdorf, Erlangen (DE); Benno Heigl, Coburg (DE); Jian Wang, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 148 days.

(21) Appl. No.: 14/339,945

(22) Filed: Jul. 24, 2014

(65) Prior Publication Data
US 2015/0030229 A1 Jan. 29, 2015

(30) Foreign Application Priority Data
Jul. 24, 2013 (DE) .................. 10 2013 214 479

(51) Int. Cl.
*G06K 9/00* (2006.01)
*A61B 6/00* (2006.01)
(Continued)

(52) U.S. Cl.
CPC ............. *A61B 6/5241* (2013.01); *A61B 6/032* (2013.01); *A61B 6/12* (2013.01); *A61B 6/487* (2013.01);
(Continued)

(58) Field of Classification Search
CPC .. G06T 2200/04; G06T 7/0032; G06T 7/0028; A61B 2019/5295; A61B 2019/5289
See application file for complete search history.

(56) References Cited

U.S. PATENT DOCUMENTS

2006/0269165 A1* 11/2006 Viswanathan ............ G06T 5/50
  382/293
2010/0160771 A1*  6/2010 Gielen ................. A61B 19/201
  600/424

(Continued)

OTHER PUBLICATIONS

A. Roche, X. Pennec, G. Malandain, and N. Ayache, "Rigid registration of 3-D ultrasound with MR images: A new approach combining intensity and gradient information", IEEE Trans. Med. Imag., vol. 20, pp. 1038-1049, 2001.*

(Continued)

*Primary Examiner* — Bhavesh Mehta
*Assistant Examiner* — Ian Lemieux
(74) *Attorney, Agent, or Firm* — Lempia Summerfield Katz LLC

(57) ABSTRACT

Methods for updating a 2D/3D registration between a three-dimensional image data set corresponding to a target area subjected to a movement and a plurality of two-dimensional projection images of the target area include: selecting a plurality of contour points along a contour, the contour being visible in a first projection image and a three-dimensional image data set registered therewith, the plurality of contour points being associated with a rigid object in the target area; determining a displacement of each contour point of the plurality of contour points between the first projection image and a successively captured second projection image; obtaining movement information for each contour point of the plurality of contour points based on the determined displacement, the movement information describing a movement of the rigid object; and updating the registration based on the obtained movement information.

17 Claims, 2 Drawing Sheets

(51) Int. Cl.
  *A61B 6/12* (2006.01)
  *A61F 2/82* (2013.01)
  *G06T 7/00* (2006.01)
  *A61B 6/03* (2006.01)
  *G06T 7/20* (2006.01)

(52) U.S. Cl.
  CPC .............. *A61B 6/501* (2013.01); *A61B 6/505* (2013.01); *A61F 2/82* (2013.01); *G06T 7/0028* (2013.01); *G06T 7/2033* (2013.01); *A61B 2090/364* (2016.02); *A61B 2090/367* (2016.02); *G06T 2207/10072* (2013.01); *G06T 2207/10121* (2013.01); *G06T 2207/10124* (2013.01); *G06T 2207/30004* (2013.01); *G06T 2207/30008* (2013.01)

(56) References Cited

U.S. PATENT DOCUMENTS

| | | | | |
|---|---|---|---|---|
| 2011/0172526 | A1* | 7/2011 | Lachaine | A61B 8/085 600/439 |
| 2013/0070995 | A1* | 3/2013 | Chou | G06T 7/0032 382/131 |
| 2015/0085981 | A1* | 3/2015 | Siewerdsen | A61B 19/5225 378/63 |

OTHER PUBLICATIONS

Brost, A. et al, "Respiratory motion compensation by model-based catheter tracking during EP procedures," Medical Image Analysis, vol. 14, No. 5, 2010, pp. 695-706.

Brost, A. et al., "Motion compensation by registration-based catheter tracking," Medical Imaging 2011: Visualization, Image-Guided Procedures, and Modeling, Mar. 1, 2011, 10 pages.

Fischler, Martin et al., "Random Sample Consensus: A Paradigm for Model Fitting with Applications to Image Analysis and Automated Cartography," Comm. of the ACM, vol. 24, No. 6, Jun. 1981, pp. 381-395.

German Office Action for German Application No. 10 2013 214 479.2, mailed Dec. 20, 2013, with English Translation.

Hartley, Richard et al., "Multiple View Geometry in Computer Vision," in Cambridge University Press, 2003, pp. 153-157 and 161-162.

Kubias, Alexander et al., "Extended Global Optimization Strategy for Rigid 2D/3D Image Registration," Computer Analysis of Images and Patterns, 2007 pp. 759-767.

Markel, J P. et al., "A review of 3D/2D registration methods for image-guided interventions," Medical Image Analysis, vol. 16 Apr. 2012, pp. 642-661.

Primoz Markel, J et al., "Robust Gradient-Based 3-D/2-D Registration of CT and MR to X-Ray Images," IEEE Transactions on Medical Imaging, vol. 27, No. 12, Dec. 2008, pp. 1704-1714.

Rohlfing et al; "Markerless Real-time 3-D Target Region Tracking by Motion Backprojection From Projection Images," IEEE Transactions on Medical Imaging; vol. 22; No. 1, 2005, pp. 1455-1468.

Wang, Jian et al., "Depth-Layer-Based Patient Motion Compensation for the Overlay of 3D Volumes onto X-Ray Sequences," Bildverarbeitung für die Medizin, 2013, pp. 128-133.

Yu Cao et al., "An Adaptive Method of Tracking Anatomical Curves in X-Ray Sequences," MICCAI, vol. 15, 2012, pp. 173-180.

* cited by examiner

METHODS FOR UPDATING 2D/3D REGISTRATION ON MOVEMENT AND COMPUTING DEVICE

RELATED APPLICATIONS

This application claims the benefit of German Patent Application No. DE 102013214479.2, filed Jul. 24, 2013. The entire contents of the priority document are hereby incorporated herein by reference.

TECHNICAL FIELD

The present teachings relate generally to methods for updating a 2D/3D registration between an initially captured three-dimensional image data set of a target area subjected to a movement that relates to the updating and a plurality of two-dimensional projection images of the target area captured during a process (e.g., a treatment process). In some embodiments, the present teachings further relate to computing devices for executing the methods.

BACKGROUND

2D/3D image fusion may be employed on a patient for radiological monitoring of interventions (e.g., treatment processes). For example, three-dimensional image data sets (e.g., CT image data sets and/or magnetic resonance image data sets) captured prior to the intervention are superimposed on two-dimensional real-time projection images (e.g., fluoroscopy images). To this end, an underlying 2D/3D registration is used. The accuracy of the superimposition directly influences the dependability of the additional information that the three-dimensional image provides.

In clinical practice, a highly accurate 2D/3D superimposition may be initially available since, for example, automatic and/or manual registration algorithms have been employed for the first projection image captured. However, there are a number of causes that may result in inaccuracies during the procedure (e.g., at least the period of time wherein projection images are captured). One of the inaccuracies relates to movement in the captured target area (e.g., the movement of a patient).

An operator involved in the process may manually initiate a new 2D/3D registration if the erroneous superimposition becomes clearly visible and affects the treatment process. The correction process that is implemented is the same registration procedure that was initially performed (e.g., using the most-recently captured projection image in order to achieve a registration with the three-dimensional image data set). However, the physician may be distracted from performing the process by the movement correction.

One solution to the problem of movement is to automatically track the movement of the patient, or at least of the captured target area, during the two-dimensional projection image capture (e.g., "on-the-fly" movement correction. Knowledge of the temporal progression of the movement may also permit predictions for further projection images. However, there is no simple solution for tracking patient movement in projection images. One reason that no such tracking is presently available is that an image datum (e.g., image value) of an X-ray projection image (e.g., a.k.a. attenuation value) is an integral of the attenuation coefficients of different depths along the path of the X-ray beam. Thus, the depth information is lost in the projection image. As a result, derivation of the three-dimensional movement from X-ray projection image sequences by tracking algorithms is difficult.

One approach is to carry out the process of 2D/3D registration as described above for each projection image captured. However, conventional methods are not sufficiently fast to permit real-time tracking of the movement and, therefore, real-time compensation for the movement. Further discussion may be found in an article by A. Kubias et al. entitled "Extended Global Optimization Strategy for Rigid 2D/3D Image Registration," in: W. G. Kropatsch, M. Kampel and A. Hanbury (Eds.): CAIP 2007, LNCS 4673, pp. 759-767, 2007.

Another approach to movement compensation involves tracking special devices (e.g., catheters) that move conjointly with an organ of a patient. In such an approach, the depth information may be obtained only when two or more projection images from different projection angles are available. Further discussion may be found in an article by P. Markelj et al. entitled "A review of 3D/2D registration methods for image-guided interventions," *Medical Image Analysis,* 2012, 16, pp. 642-661.

Another approach is to obtain the depth information from the initial registration. The target area is broken down into different depth layers. A standard tracking method is associated with movement estimation effective at depth. The 3D movement is automatically detected and compensated for, thereby facilitating a correct superimposition. Further discussion may be found in an article by J. Wang et al. entitled "Depth-Layer-Based Patient Motion Compensation for the Overlay of 3D Volumes onto X-Ray Sequences," in: H.-P. Meinzer et al. (publisher), Bildverarbeitung für die Medizin 2013, Informatik aktuell, Springer Verlag Berlin Heidelberg 2013, pp. 128-133. However, in this approach, normal tracking algorithms are not suitable for X-ray projection images.

SUMMARY AND DESCRIPTION

The scope of the present invention is defined solely by the appended claims, and is not affected to any degree by the statements within this summary.

In some embodiments, a method for improved estimation of the three-dimensional movement of a target area during capture of two-dimensional projection images is provided that permits an accurate updating of a 2D/3D registration.

In accordance with the present teachings, a plurality of contour points lying along a contour is selected. The contour is visible in the projection image and the three-dimensional image data set registered therewith. The contour is associated with a rigid object in the target area.

A displacement of the contour points in the projection images is ascertained between a pair of successively captured projection images obtained from the moving target area.

Movement information describing the movement of the rigid object is ascertained by restricting the degrees of freedom of movement to observable movements perpendicular to the course of the contour in the three-dimensional image data set. A system of equations resulting from three-dimensional target planes wherein the displaced contour point lies is solved. The movement information is ascertained for each contour point based on the displacement.

The registration is updated in accordance with the movement information.

In accordance with the present teachings, clearly recognizable contours in the two-dimensional projection image (e.g., boundaries between clearly different image values or contrasts) may be used for tracking because the three-dimensional position of the corresponding contour points is known at least for a first projection image. A system of equations may be derived from the projection geometry known for capture of the projection images and from the relationships of the contour described by the contour points. Although the system of equations may not be solved unambiguously for one contour point, the system of equations becomes solvable for the plurality of contour points in accordance with the present teachings. An assumption is made that the observed contour is associated with a rigid object in the target area. Accordingly, the rigid object does not deform and, therefore, moves the same at each contour point. If parameters that describe the movement of the rigid object are applied in the movement information, the resulting system of equations may be solved. As described above, it is assumed that the projection geometry for the projection images (e.g., X-ray projection images) is known. As a result, a common coordinate system may be defined based on the existing 2D/3D registration. In the coordinate system, the structures of the three-dimensional image data set and the image plane of the two-dimensional projection images may be observed and a mathematical description may be derived, as further described below. In some embodiments, a fan-beam geometry may be used for capturing the projection images.

Rigid objects in target areas (e.g., inside a patient undergoing treatment and/or diagnosis) may be observed. In some embodiments, the rigid object may correspond to an anatomical feature (e.g., at least a bone, such as a skull). In other embodiments, the rigid object may correspond to a medical instrument introduced into the patient (e.g., a stent or a marker device). Many target areas and tasks (e.g., imaging in the region of the skull) may facilitate observation of the contours occurring in the image (e.g., pronounced differences in contrast or image value) since the entire target area may be perceived as a conjointly moving, rigid object. In accordance with the present teachings, instead of using landmarks (e.g., a tip of a catheter), any rigid part of the body may be used (e.g., bones that are clearly visible as the most likely expected rigid structure in an X-ray projection image, such as bone structures surrounded by an aqueous environment). To minimize confusion with introduced instruments and the like, a segmentation may be performed in the three-dimensional image data set (e.g., separately according to different tissue types and the like).

In some embodiments, the above-described first projection image may be the image that initially served as the basis for the original 2D/3D registration (e.g., the first two-dimensional projection image captured or the two-dimensional projection image captured in the event of a re-triggering of the 2D/3D registration). In accordance with the present teachings, the movement may be tracked in stepwise fashion (e.g., from projection image to projection image) since, as a result of the updating, the 2D/3D registration is always known for the projection image captured first in the pair of most-recently-captured projection images. This projection image may serve as the first projection image. Thus, a series of projection images may be captured. The movement information may be ascertained for each pair of successively measured projection images and used for updating the registration and the three-dimensional position of the contour points. An underlying, original 2D/3D registration may take place on the basis of a first projection image, whereupon tracking may then occur from projection image to projection image. The information of the projection images may also be observed along the entire sequence. Better estimates of a continuous movement may be performed if the previous movement sequence is known. In accordance with the present teachings, the 2D/3D registration may be kept updated step-by-step.

In accordance with the present teachings, movement information may be obtained for each projection image based on a comparison with the preceding projection image. The approach provides a rapid calculation that may be performed in real time. In accordance with the present teachings, only a few areas of the two-dimensional projection image (e.g., the contour points on the at least one contour) are observed. A closed form of equations (e.g., linear equations that may be solved by classic optimization algorithms) may be derived, as described below.

The direction perpendicular to the course of the contour corresponds to the gradient in the three-dimensional image data set at the corresponding contour point. In accordance with the present teachings, gradient-based methods for the automatic compensation of movements in the target area may be provided. In the local vicinity of a contour point, a small movement of the rigid object results in a change in only the gray values at the same location if the movement has a component in the direction of the gradient vector g=∇f(w). In this expression, f specifies the image function (e.g., function of the image values) of the three-dimensional image data set, and w specifies the vector to a contour point W. All movements that occur perpendicular to g do not change the gray values in the proximity of the point W. However, a movement dp of the contour point P corresponding to the three-dimensional contour point W may only be determined in the projection image if the movement has components in the direction of the projection image gradient vector ∇I(p). In this expression, I denotes the function of the image values (e.g., image function) for the projection image. The vectors dp and g are coplanar because both vectors are linked with one another on the basis of the same contour. As a result, only movements in the directions of the two-dimensional and the three-dimensional image gradients may be observed.

The two-dimensional and three-dimensional movements are linked with one another by the target plane π that contains the target point of the movement w+dw (e.g., the new three-dimensional position of the contour point W after the movement), the projection center C (e.g., the focus of the radiation source that may be chosen as the origin of the coordinate system), and the moving two-dimensional contour point p+dp. Based on geometrical considerations, a normal vector of the target plane π may be determined.

A normal vector of the target plane may be formed as the cross product of (a) a vector that is itself formed as a cross product of a contour vector standing perpendicular to the course of the contour in the three-dimensional image data set with the vector describing the three-dimensional position of the contour point prior to the movement with (b) the summation vector of the contour point prior to the movement on the image plane and the vector describing the displacement in the image plane. The contour vector may be determined as the gradient of the image data of the three-dimensional image data set at the contour point. Using the naming conventions introduced above, the normal vector n of the target plane π may be given as in EQN. (1):

$$n = \frac{(w \times g) \times (p + dp)}{\|(w \times g) \times (p + dp)\|}. \qquad (1)$$

If the projection center C is situated in the origin, as described above, EQN. (2) may be written for the most-recently sought, moving three-dimensional contour point w+dw:

$$n^T(w+dw)=0. \tag{2}$$

The system of equations may be adjusted to zero based on the setting of the scalar product of the normal vector with a vector that is formed as the sum of (a) the vector describing the three-dimensional position of the contour point prior to the movement and (b) the sought vector describing the three-dimensional displacement of the contour point caused by the movement. A linear relationship is thus given.

To further simplify the calculation, an assumption may be made that a rotational component of the movement is linear to obtain a linear equation system. Thus, for a small movement (e.g., when projection images are captured at a high rate), the differential movement dw of the contour point W may be written as shown in EQN. (3) below:

$$dw = d\omega \times w + dv. \tag{3}$$

In EQN. (3), dω corresponds to the differential rotation about the origin and dv corresponds to the differential linear movement. If EQN. (3) is now inserted into EQN. (2), the following expression is obtained:

$$n^T(d\omega \times w) + n^T dv + n^T w = 0$$

$$(n \times w)^T d\omega - n^T d_v = n^T w.$$

As a result, the description of the desired linear equation system for dω and dv may be expressed as shown in EQN. (4):

$$\begin{pmatrix} n \times w \\ -n \end{pmatrix}^T \begin{pmatrix} d\omega \\ dv \end{pmatrix} = n^T w. \tag{4}$$

If only one contour point W were to be observed, the system of equations in EQN. (4) would be under-determined. However, a plurality of contour points W is observed. The movement of the plurality of contour points W may be described by dω and dv. Accordingly, normal solution methods for linear equation systems may be used.

In summary, movement information may be described by the parameters dω and dv. The movement information may be ascertained by the following acts. In a first act, two (e.g., X-ray) projection images of the same target area containing a rigid object are captured before and after a small movement. The projection geometry and a 2D/3D registration with a three-dimensional image data set (e.g., that may itself already be updated by previous ascertainment of movement information) are known. A plurality of contour points $W_i$ in the three-dimensional data set and the corresponding two-dimensional contour points $P_i$ in the earlier-captured projection image are then ascertained. In a third act, the displacement $dp_i$ of the contour points $P_i$ in the projection images is ascertained. The implementation of acts 2 and 3 is further described below. The gradient vectors (e.g., contour vectors) $g_i$ for the different contour points $W_i$ may be calculated from the three-dimensional image data set or the corresponding image values. In a fifth act, the normal vectors $n_i$ may be ascertained from the gradient vectors in accordance with EQN. (1) for each target plane $p_i$. The linear system of equations is formed in accordance with EQN. (4) and solved for the variables dω and dv. The movement information obtained by solving the system of equations may be utilized in to update the 2D/3D registration. As described above, the method may be repeated for each newly captured projection image in a series of projection images since geometrical relationships vis-à-vis a predecessor projection image are known as a result of the updating.

In some embodiments, a RANSAC algorithm is used for solving the equation system in order to better detect deviating input values or solutions (e.g., outliers). RANSAC algorithms are widely used as described, for example, in (a) the book by R. Hartley et al. entitled *Multiple View Geometry in computer vision (Second Edition)*, Cambridge University Press, 2003, pp. 153-157, 161-162, and (b) the article by N. Fischler et al. entitled "Random Sample Consensus: A Paradigm for Model Fitting with Applications to Image Analysis and Automated Cartography," *Comm. of the ACM*, 1981, Vol. 24, pp. 381-395.

In some embodiments, as described above, a three-dimensional coordinate system may be used having its origin at the focal point of a radiation source that is employed for capturing the projection images.

As described above, the focal points in both the three-dimensional image data set ($W_i$) and the two-dimensional projection image ($P_i$) are detected. In some embodiments, an unambiguous, clear assignment may naturally be present. In some embodiments, the contour points may be detected initially in the three-dimensional image data set and then assigned to corresponding contour points in the two-dimensional projection image. In some embodiments, contour points in the three-dimensional space may be deduced from contour points in the two-dimensional projection image.

The contour points may be initially selected in the first projection image in order thereafter to ascertain the three-dimensional position of the contour points by taking into consideration at least one forward projection from the three-dimensional image data set. However, in accordance with the present teachings, the three-dimensional position of the contour points may be ascertained after selection of the contour points in the first projection image by taking into consideration a division of the three-dimensional image data set into depth sections. A method that uses such depth sections is described in the above-cited article by J. Wang et al. entitled "Depth-Layer-Based Patient Motion Compensation for the Overlay of 3D Volumes onto X-Ray Sequences." The thickness of the depth sections may be chosen to be extremely thin to provide maximize the accuracy of the determination of the three-dimensional position of focal points in the three-dimensional image data set. Contour points in the three-dimensional image data set may also be used as the basis for an application of the method described in the article by J. Wang. Other known methods may likewise be used to determine the position of the contour points in both the two-dimensional projection image and the three-dimensional image data set.

A tracking technique for a contour may be used to ascertain the displacement. Conventional tracking techniques or tracking algorithms are optimized to the target of the tracking of a set of structure points (e.g., contour points), such that an optimization may also be performed for X-ray sequences. Such an optimized approach has already been proposed in an article by Yu Cao and Peng Wang entitled "An Adaptive Method of Tracking Anatomical Curves in X-Ray Sequences," *MICCAI*, 2012, pp. 173-180, and may be used in accordance with the present teachings.

In some embodiments, methods for optical flow (e.g., such as may be employed in total for optical images of a sequence) may be applied to X-ray projection image sequences. The contour line, due to its special properties, may behave like a structure captured using a conventional optical camera. Thus, the methods for optical flow may be employed at least to a limited extent for the points. For example, assuming a linear approximation of the image value function, the displacement in the image plane may be ascertained for the image data from the product of (a) the negative change in intensity at the contour point in the projection image prior to the movement, and (b) the inverse of the gradient of the image function at the contour point in the projection image prior to the movement. The product may be expressed as shown in EQN. (5):

$$\begin{pmatrix} dp_x \\ dp_y \end{pmatrix} = dp = -dI \cdot (\nabla I)^{-1}. \qquad (5)$$

In EQN. (5), I again represents the image value function in the projection image. Thus, the method may be implemented simply (e.g., in computing terms).

An iterative ascertainment of the displacement may be undertaken by using the most-recently ascertained displacement for the contour points in order to ascertain first potential moving contour points. The first potential moving contour points are compared with the measured moving contour points of the projection image after the movement in order to ascertain a correction displacement. Because a linear approximation of the image function has been performed in the projection image, the error occurring as a result may be corrected by iteratively repeating the process. When a first result is available for the movement, the target position in the projection image resulting therefrom may be calculated for each contour point. If the differences from the projection image captured later are observed at this stage, a correction displacement may be added additively to the most-recently ascertained displacement. The correction displacement may likewise be determined using EQN. (5), and additional iterations may follow.

As described above, methods in accordance with the present teachings may be used for superimposition tasks (e.g., during a medical intervention). By using the updated 2D/3D registration, a superimposed representation of the three-dimensional image data set and the very latest projection image may be ascertained and displayed.

In some embodiments, the present teachings also relate to a computing device that may be configured as part of an X-ray unit. The computing device is configured to execute a method in accordance with the present teachings. All embodiments relating to methods in accordance with the present teachings may likewise be applied analogously to computing devices in accordance with the present teachings.

A computing device may contain a selection unit configured to select a plurality of contour points lying along a contour visible in a first projection image and the three-dimensional image data set registered therewith. The contour may be associated with a rigid object in the target area. In addition, a displacement detection unit may be used to ascertain the displacement of contour points between two projection images captured in succession from the moving target area. A movement information detection unit configured to solve the system of equations to ascertain the movement information may also be part of the computing device. The computing device may further include an updating unit for the registration configured to uses the movement information in order to update the 2D/3D registration.

In some embodiments, methods in accordance with the present teachings may be implemented by a computer program that executes the acts of the method when it runs on a computing device (e.g., a computing device in accordance with the present teachings). Such a computer program may be stored on a non-transitory storage medium (e.g., a CD-ROM).

DETAILED DESCRIPTION

Figure 1:
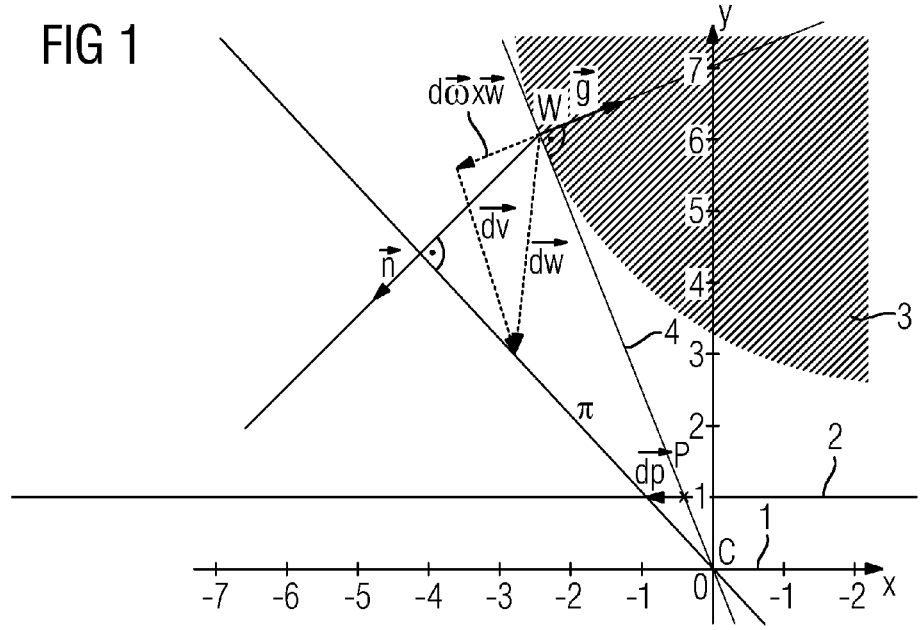
FIG. 1 shows a diagram of an example of a derivation of a method in accordance with the present teachings.

FIG. 1 shows an example of geometrical considerations that underlie methods in accordance with the present teachings, and explains the derivation and notations used herein. An x-y plane of a coordinate system 1 is shown wherein both the position of the three-dimensional image data set and the position of at least the first projection image are known (e.g., based on the 2D/3D registration known for the first projection image). The above-described gradient vector g lies in the plane in FIG. 1. Points are represented by uppercase letters (e.g., the contour points W, P in the three-dimensional image data set or in the two-dimensional projection image). Vectors are shown by boldfaced lowercase letters. The vectors may be assumed to be column vectors, such that the scalar product between two vectors a and b results in $a^T b$.

As shown in FIG. 1, the origin of the coordinate system 1 is chosen as the focal point C of the X-ray radiation source and used as the projection center. The image plane 2 may be chosen for the sake of simplicity as having a z value of 1. Thus, a point P of the projection image may be regarded as a three-dimensional point that contains a z value of 1 and x and z values corresponding to the coordinates in the projection image.

FIG. 1 also shows a rigid object 3 in the target area to be captured. When the rigid object 3 is irradiated, the rigid object 3 exhibits a contour that may run perpendicular to the plane of FIG. 1 in the emerging projection image. Part of the contour is the contour point P that is also correspondingly contained as point W in the three-dimensional image data set captured in advance (e.g., a CT image data set or an MR image data set). Because, as described above, the three-dimensional image data set and at least one first projection image are registered with one another by the 2D/3D registration, the points of the three-dimensional image data set and the at least one first projection image may be represented in the common coordinate system 1. Therefore, the contour point W in the three-dimensional image data set lies on a contour and is projected in accordance with the indicated beam path 4 onto the contour point P in the two-dimensional projection image (e.g., in other words, in the image plane 2). The projection results therefore based on the equation $p = w/w_z$.

Since fluoroscopy X-ray images may be observed as two-dimensional projection images, the fluoroscopy X-ray images are captured by an X-ray arrangement having an X-ray radiation source (with focal point C) and an X-ray detector. The projection geometry of the X-ray arrangement may be described by a projection matrix $M = K(R|t)$. A point having the image coordinates u, v may be transformed into camera coordinates p via EQN. (6):

$$p = K^{-1} \overline{\begin{pmatrix} u \\ v \\ 1 \end{pmatrix}}. \qquad (6)$$

In EQN. (6), the horizontal bar signifies that the z component of the vector is normalized to 1. Coordinates in the world coordinate system are converted using the rotation R and the translation t into the camera coordinates (e.g., in other words, the coordinate system 1). The camera coordinates has an origin at the focal point (projection center C) of a radiation source employed for capturing the projection images (e.g., an X-ray radiation source). As described above, the origin is then part of the target plane π and the calculations are greatly simplified. To further simplify calculations, the image plane 2 is assumed to lie, for example, at "1" in the corresponding coordinate. The image plane 2 may not be defined by a radiation detector or the actual position thereof. Thus, a rescaling may be performed without difficulty.

Only contour points W that lie on superimposed contours (e.g., contour points that also appear in the projection image as a contour—in other words, the edge of a region exhibiting a noticeably different attenuation value or image value than its surroundings) may be observed. An example of an object 3 having contours that are clearly visible in X-ray projection images are bone structures that are surrounded by aqueous environments. The points may be identified from the three-dimensional image data set (e.g., a reconstructed CT volume) and correlated with points on the contour in an X-ray projection image, as described above.

The geometrical relationship between the three-dimensional image data set and the projection image captured at an earlier time is known by two projection images described as the projection matrix M. Consequently, a 2D/3D registration may already be available, for example, by capturing the three-dimensional image data set as a CT image data set in a calibrated system or by performing a normal registration process. Moreover, following a very small movement, a second X-ray projection image may be captured. Thus, a pair of projection images is present. The first projection image is registered with the three-dimensional image data set but the second projection image is no longer registered because a movement (albeit a small movement) of the target area has occurred.

A small, differential movement of a contour point W may be denoted as dw and may be described by EQN. (3). The movement information to be determined later is formed by dω as differential rotation about the origin and dv as differential linear movement (e.g., translation). In FIG. 1, the vectors dw, dω×w, and dv are drawn as dotted lines to indicate that the vectors lie outside the plane of representation described by C, W, and the gradient vector g.

Within a local vicinity of the focal point W, a small movement of the object 3 results only in a change in the gray values at the same location if the movement exhibits a component in the direction of the gradient vector g. As described above, the gradient vector g may be calculated for each focal point W from the image data of the three-dimensional image data set described by the three-dimensional image function. All movements that run orthogonal to g do not change the gray values in the proximity of the point W. Accordingly, a movement dp of the point P in the projection image may be determined if the movement occurs in the direction of the projection image gradient vector VI(p). Since the vectors dp and g are both derived from the same contour, the vectors are coplanar. As a result, only movements in the direction of the two-dimensional and the three-dimensional gradient of the image data may be observed.

The two-dimensional and the three-dimensional movements are linked with one another by the target plane π shown in FIG. 1. In addition to the target point of the movement, w+dw, the target plane π contains the projection center C and the moving contour point in the projection image, p+dp.

The normal vector n of the target plane π is also shown in FIG. 1 and may be determined using EQN. (1). The linear system of equations provided in EQN. (4) results in the condition expressed in EQN. (2).

Based on the above findings, a representative method in accordance with the present teachings will now be described in reference to FIG. 2.

Figure 2:
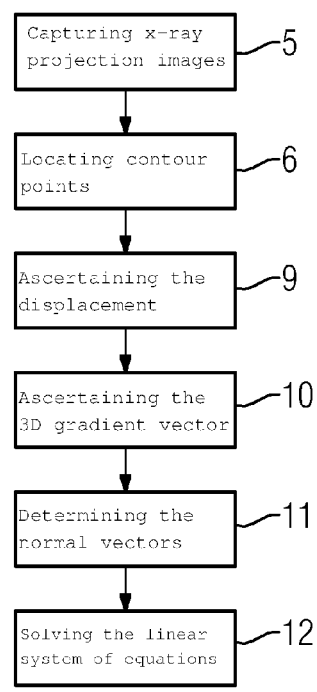
FIG. 2 shows a flowchart of an exemplary method in accordance with the present teachings.

In act 5 of FIG. 2, two X-ray projection images of the same target area are initially captured before and after a small movement. For the first of the projection images, the projection geometry and, in some embodiments, the 2D/3D registration with the three-dimensional image data set are known.

In act 6 of FIG. 2, the contour points $W_i$ in the three-dimensional image data set and the corresponding contour points $P_i$ in the first projection image are located. Methods may be used wherein the points in the projection image may be located by forward projections having a known beam path. Alternatively, methods using depth sections (e.g., depth layers) may be used, as described, for example, in the above-cited article by J. Wang.

Figure 3:
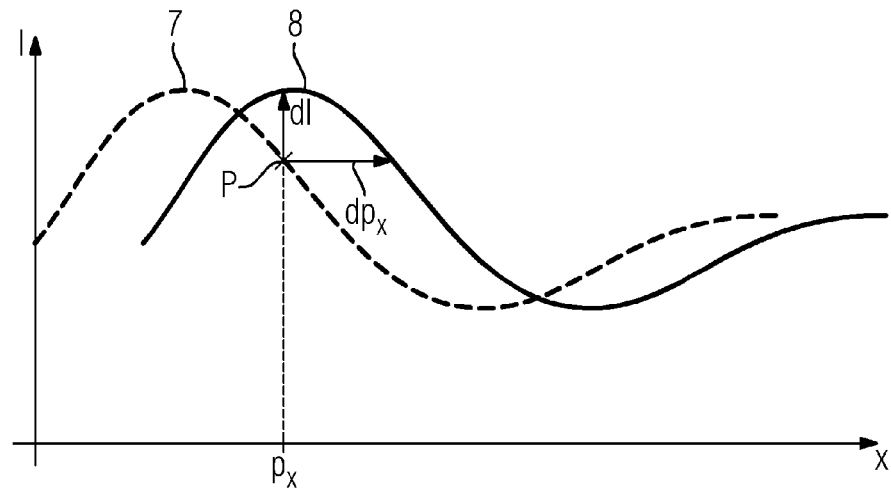
FIG. 3 shows a diagram of exemplary tracking of a contour in two-dimensional projection images.

The displacement of the contour points $P_i$ in the projection images from the first projection image into the second projection image is determined. Tracking techniques, such as those described, for example, in the article by Yu Cao and Peng Wang, may be employed. In some embodiments, relationships derived from the methods for determining optical flow in order to determine the displacement dp may be used, as further described in reference to FIG. 3. In FIG. 3, the curve 7 for the image data of the first projection image and the curve 8 for the image data of the second projection image are represented along the direction x as the image value function I. Prior to the movement, the contour point P was situated at the coordinate $p_x$. As a result of the movement, the contour point P is displaced by $dp_x$. A change in intensity dI occurs at the point $p_x$. If the image function I is linearly approximated, the displacement dp may be determined according to EQN. (5).

In order to counteract errors caused by the linear approximation correction, the displacement ascertained in the previous act may be applied to the contour points $P_i$ experiencing no movement. The emerging contour may be compared with the contour actually measured in the second projection image. If there are differences, EQN. (5) may be used to ascertain a displacement correction. The displacement correction may be added to the previous displacement in order to obtain a new, corrected displacement until a termination condition is given. The iterative correction may be carried out on the basis of the course of the contour that may be detected in both projection images. Consequently, the linkage between the points that is given by the rigid 3D movement is taken into consideration, in contrast to an iteration of the EQN. (5) for each individual point.

In third act 9 in FIG. 2, the displacement is ascertained.

In fourth act 10 in FIG. 2, the three-dimensional gradient vector $g_i$ is ascertained from the image data of the three-dimensional image data set.

In fifth act 11 in FIG. 2, the normal vectors $n_i$ according to EQN. (1) may be determined. In sixth act 12 in FIG. 2, the linear system of equations expressed in EQN. (4) may be formed and may be solved by corresponding solution algorithms vis-à-vis the movement information (e.g., the parameters dω and dv). RANSAC algorithms may be used to detect so-called "outliers."

Updating of the 2D/3D registration takes place from the movement information ascertained as described above. Therefore, the geometrical relationship between the second projection image and the three-dimensional image data set is now known. An entire series of two-dimensional projection images may be captured, for example, during a medical intervention. A method in accordance with the present teachings may be repeated for each pair of projection images. The second projection image in the previous block may later form the new first projection image. The projection image captured immediately thereafter becomes the new second projection image. The displacements are ascertained again, and the system of equations is solved. Items of information (e.g., contour points $W_i$, $P_i$, gradient, and the like) that are already known from the process may not be ascertained again. Thus, the movement of the rigid object 3 and the target area may be constantly tracked rapidly and in real-time. Since X-ray projection images for monitoring a medical intervention may be captured at a high rate, the condition of small movements (and, therefore, the approximation in EQN. (3)) may be met.

The ascertained movement information for each pair of projection images may also be stored in order, for example, to analyze the information (e.g., to identify a better starting point for the solution of EQN. (4) when a relatively uniform movement is occurring, and the like). The movement information of the preceding pairs may be taken into consideration when choosing a starting point for the solution of the equation system in EQN. (4).

By updating the 2D/3D registration in accordance with the present teachings, a qualitatively excellent superimposition of two-dimensional and three-dimensional image data may take place to support a person performing an intervention.

Figure 4:
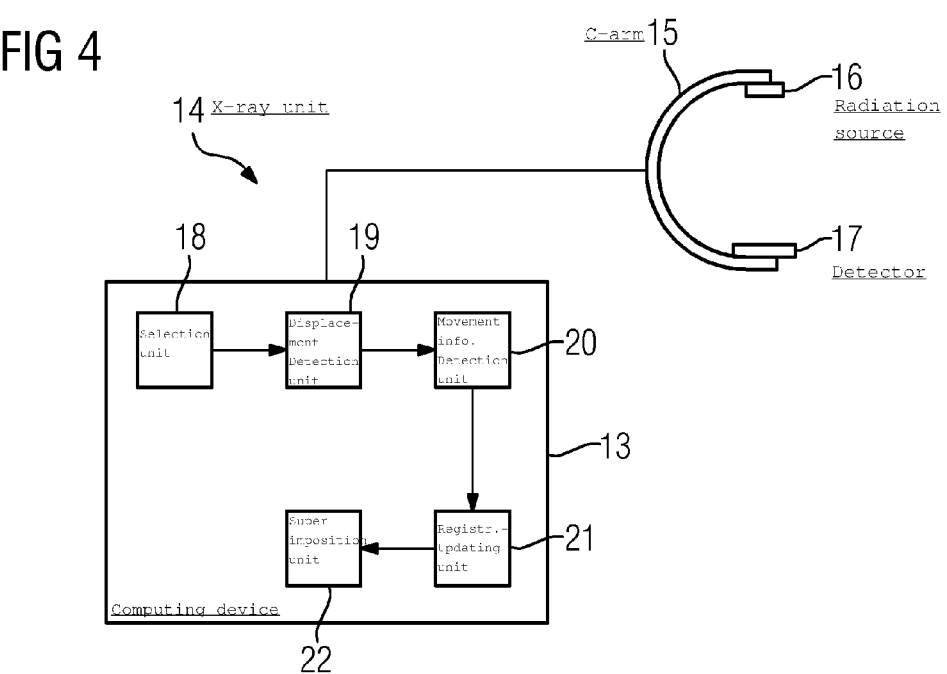
FIG. 4 shows an example of a computing device in accordance with the present teachings.

FIG. 4 shows a schematic diagram of an example of a computing device 13 in accordance with the present teachings. The computing device 13 forms part of an X-ray unit 14. The computing device 13 is configured to evaluate data delivered, for example, by a capture arrangement arranged on a C-arm 15 that includes an X-ray radiation source 16 and an X-ray radiation detector 17. The computing device 13 is configured to execute a method in accordance with the present teachings. The computing device 13 includes a selection unit 18 configured to locate the contour points $W_i$ and $P_i$ in the three-dimensional image data set and in the two-dimensional projection image, and to correctly assign the contour points to one another.

The computing device 13 further includes a displacement detection unit 19 configured to ascertain the displacements of the contour points in the projection images as shown, for example, in FIG. 3.

A movement information detection unit 20 is configured to ascertain the movement information by setting up and solving the equation system in EQN. (4). The updating of the 2D/3D registration may take place in a registration-updating unit 21. The computing device 13 may also include a superimposition unit 22 configured to provide a superimposed representation of the most-recent projection image and the three-dimensional data set based on the updated 2D/3D registration.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A method for updating a 2D/3D registration between a three-dimensional image data set corresponding to a target area and a plurality of two-dimensional projection images of the target area, the target area being subjected to a movement, the method comprising:

capturing, using an X-ray unit, the plurality of two-dimensional projection images of the target area;

selecting, by a selection unit of a computing device, a plurality of contour points along a contour associated with a rigid object in the target area, the contour being visible in a first captured projection image and a three-dimensional image data set registered therewith;

determining, by a displacement detection unit of the computing device, a displacement of each contour point of the plurality of contour points between the first captured projection image and a successively captured second projection image;

obtaining, by a movement information detection unit of the computing device, movement information for each contour point of the plurality of contour points based on the determined displacement, the movement information describing a movement of the rigid object, wherein the obtaining comprises (1) restricting degrees of freedom of movement to observable movements that are perpendicular to a course of the contour in the three-dimensional image data set, and (2) solving a system of equations for a three-dimensional target plane that comprises the displaced contour point;

forming a normal vector of the three-dimensional target plane, wherein the normal vector comprises a cross product of a first vector and a summation vector, wherein the first vector is formed as a cross product of a contour vector that stands perpendicular to the course of the contour in the three-dimensional image data set with a second vector that describes a three-dimensional position of a contour point prior to the movement, and wherein the summation vector comprises the contour point prior to movement on an image plane and a third vector describing a displacement in the image plane; and updating, by a registration-updating unit of the computing device, the registration based on the obtained movement information.

2. The method of claim 1, further comprising adjusting the system of equations to zero based on a setting of a scalar product of the normal vector with a fourth vector, wherein the fourth vector is formed as a sum of (a) the second vector that describes the three-dimensional position of the contour point prior to the movement and (b) a sought vector that describes a three-dimensional displacement of the contour point caused by the movement.

3. The method of claim 2, further comprising determining the contour vector as a gradient of the image data of the three-dimensional image data set at the contour point.

4. The method of claim 2, further comprising assuming that a rotational component of the movement is linear to obtain a linear system of equations.

5. The method of claim 1, further comprising determining the contour vector as a gradient of the image data of the three-dimensional image data set at the contour point.

6. The method of claim 1, further comprising assuming that a rotational component of the movement is linear to obtain a linear system of equations.

7. The method of claim 1, further comprising using a random sample consensus (RANSAC) algorithm for the solving of the system of equations.

8. The method of claim 1, further comprising using a three-dimensional coordinate system having an origin that corresponds to a focal point of a radiation source that is used to capture the plurality of two-dimensional projection images.

9. The method of claim 1, wherein the plurality of contour points is initially selected in the first captured projection image, the method further comprising determining a three-dimensional position of each contour point of the plurality of contour points based on (a) at least one forward projection from the three-dimensional image data set, (b) a division of the three-dimensional image data set into a plurality of depth sections, or (c) at least one forward projection from the three-dimensional image data set and the division of the three-dimensional image data set into the plurality of depth sections.

10. The method of claim 1, wherein the rigid object comprises a bone, a medical instrument introduced into a patient, or a combination thereof.

11. The method of claim 10, wherein the bone comprises a skull, and wherein the medical instrument comprises a stent or a marker device.

12. The method of claim 1, further comprising capturing the plurality of two-dimensional projection images, obtaining movement information for each pair of successively measured projection images in the plurality of two-dimensional projection images, and updating the registration and three-dimensional position of each contour point of the plurality of contour points based on the obtained movement information.

13. The method of claim 1, further comprising determining and displaying a superimposed representation of the three-dimensional image data set and a most recent projection image.

14. The method of claim 1, wherein the plurality of two-dimensional projection images of the target area is captured during a treatment process.

15. A method for updating a 2D/3D registration between a three-dimensional image data set corresponding to a target area and a plurality of two-dimensional projection images of the target area, the target area being subjected to a movement, the method comprising:
  capturing, using an X-ray unit, the plurality of two-dimensional projection images of the target area;
  selecting, by a selection unit of a computing device, a plurality of contour points along a contour associated with a rigid object in the target area, the contour being visible in a first captured projection image and a three-dimensional image data set registered therewith;
  determining, by a displacement detection unit of the computing device, a displacement of each contour point of the plurality of contour points between the first captured projection image and a successively captured second projection image, wherein the determining of the displacement in an image plane comprises assuming a linear approximation of an image value function for image data, and calculating a product of (a) a negative change in intensity at a contour point in a projection image prior to the movement, and (b) an inverse of a gradient of the image value function at the contour point in the projection image prior to the movement;
  obtaining, by a movement information detection unit of the computing device, movement information for each contour point of the plurality of contour points based on the determined displacement, the movement information describing a movement of the rigid object, wherein the obtaining comprises (1) restricting degrees of freedom of movement to observable movements that are perpendicular to a course of the contour in the three-dimensional image data set, and (2) solving a system of equations for a three-dimensional target plane that comprises the displaced contour point; and
  updating, by a registration-updating unit of the computing device, the registration based on the obtained movement information.

16. The method of claim 15, wherein the determining of the displacement is iterative and further comprises:
  using a most-recently-determined displacement of the contour point as a first potential moving contour point;
  comparing the first potential moving contour point with a measured moving contour point of the projection image after the movement, thereby determining a correction displacement; and
  adding the correction displacement to the most-recently-determined displacement, thereby determining a current displacement.

17. An x-ray unit comprising a computing device configured to update a 2D/3D registration between a three-dimensional image data set corresponding to a target area and a plurality of two-dimensional projection images of the target area, the target area being subjected to a movement, the computing device of the x-ray unit configured to:
  select a plurality of contour points along a contour associated with a rigid object in the target area, the contour being visible in a first projection image and a three-dimensional image data set registered therewith;
  determine a displacement of each contour point of the plurality of contour points between the first projection image and a successively captured second projection image;
  obtain movement information for each contour point of the plurality of contour points based on the determined displacement, the movement information describing a movement of the rigid object, wherein the movement information detection unit is configured to (1) restrict degrees of freedom of movement to observable movements that are perpendicular to a course of the contour in the three-dimensional image data set and (2) solve a system of equations for a three-dimensional target plane that comprises the displaced contour point;

form a normal vector of the three-dimensional target plane, wherein the normal vector comprises a cross product of a first vector and a summation vector, wherein the first vector is formed as a cross product of a contour vector that stands perpendicular to the course of the contour in the three-dimensional image data set with a second vector that describes a three-dimensional position of a contour point prior to the movement, and wherein the summation vector comprises the contour point prior to movement on an image plane and a third vector describing a displacement in the image plane; and update the registration based on the obtained movement information.

\* \* \* \* \*